United States Patent
Bosetti et al.

(10) Patent No.: US 8,969,605 B2
(45) Date of Patent: Mar. 3, 2015

(54) PROCESS FOR THE PRODUCTION OF BIO-OIL FROM MUNICIPAL SOLID WASTE

(75) Inventors: Aldo Bosetti, Vercelli (IT); Giuliana Franzosi, Novara (IT)

(73) Assignee: ENI S.p.A., Rome (IT)

( * ) Notice: Subject to any disclaimer, the term of this patent is extended or adjusted under 35 U.S.C. 154(b) by 296 days.

(21) Appl. No.: 13/640,910

(22) PCT Filed: Mar. 30, 2011

(86) PCT No.: PCT/IB2011/000693
§ 371 (c)(1),
(2), (4) Date: Nov. 26, 2012

(87) PCT Pub. No.: WO2011/128741
PCT Pub. Date: Oct. 20, 2011

(65) Prior Publication Data
US 2013/0090487 A1   Apr. 11, 2013

(30) Foreign Application Priority Data
Apr. 15, 2010   (IT) ............... MI2010A0646

(51) Int. Cl.
C11B 13/00 (2006.01)
C12P 7/64 (2006.01)
(Continued)

(52) U.S. Cl.
CPC ............ *C12P 7/6409* (2013.01); *C02F 1/281* (2013.01); *C02F 1/42* (2013.01); *C02F 3/28* (2013.01); *C02F 3/341* (2013.01); *C02F 3/347* (2013.01); *C02F 11/18* (2013.01); *C10G 1/02* (2013.01);
(Continued)

(58) Field of Classification Search
USPC .................. 554/177, 191; 435/134
See application file for complete search history.

(56) References Cited

U.S. PATENT DOCUMENTS

2004/0034262 A1   2/2004   Van de Beld et al.
2005/0177013 A1   8/2005   Countz
(Continued)

FOREIGN PATENT DOCUMENTS

EP   1 184 443         3/2002
EP   1184443 A1 *   3/2002   ............... C10G 1/00
(Continued)

OTHER PUBLICATIONS

Nuovo Colombo: "Il Manuale dell'Ingegnere", Editore Ulrico Hoepli,Mi lano, 84ma edizione, 2003, Volume Terzo, Section "Q. Ingegneria Ambientale", Chapter "4. Oepurazione delle Acque di Rifiuto", Paragraphs "4.5 Trattamenti Secondari ", p. Q-117-Q-146, "4.7 Trattamenti Cimico-Fisici", p. Q-170-Q-184, and "4.8 Trattamento dei fanghi", pagg.*

Vismara, R., et al.,"4.5 Trattamenti Secondari," Nuovo Colombo Il Manuale dell Ingegnere, vol. 3, pp. Q117-Q146 and Q170-216, XP-002615375, (2003).

International Search Report Issued Aug. 3, 2011 in PCT/IB11/00693 Filed Mar. 30, 2011.

*Primary Examiner* — Deborah D Carr

(74) *Attorney, Agent, or Firm* — Oblon, McClelland, Maier & Neustadt, L.L.P.

(57) ABSTRACT

A process for producing bio-oil from municipal solid waste, the process including: a) liquifying municipal solid waste, to obtain a mixture containing an oily phase containing bio-oil, a solid phase, and a first aqueous phase; b) treating the first aqueous phase from a) with an adsorbing material, to obtain a second aqueous phase; c) fermenting the second aqueous phase from b), to obtain a biomass; d) subjecting the biomass obtained in c) to the liquification a). The bio-oil obtained is advantageously used in the production of biofuels for motor vehicles or for the generation of electric energy or heat.

32 Claims, 1 Drawing Sheet

(51) Int. Cl.
*C02F 1/28* (2006.01)
*C02F 1/42* (2006.01)
*C02F 3/28* (2006.01)
*C02F 3/34* (2006.01)
*C02F 11/18* (2006.01)
*C10G 1/02* (2006.01)
*C10L 3/08* (2006.01)
*C10L 5/46* (2006.01)

(52) U.S. Cl.
CPC ... *C10L 3/08* (2013.01); *C10L 5/46* (2013.01); *C02F 2301/066* (2013.01); *C02F 2303/10* (2013.01); *Y02E 50/30* (2013.01); *C10G 2300/1011* (2013.01); *C10G 2300/1014* (2013.01); *Y02E 50/10* (2013.01)
USPC .......................... 554/177; 554/191; 435/134

(56) References Cited

U.S. PATENT DOCUMENTS

| | | |
|---|---|---|
| 2007/0043246 A1 | 2/2007 | Bridle |
| 2007/0209999 A1 | 9/2007 | Smith et al. |
| 2011/0294175 A1 | 12/2011 | Bellussi et al. |
| 2012/0172642 A1 | 7/2012 | Bosetti et al. |

FOREIGN PATENT DOCUMENTS

| | | | |
|---|---|---|---|
| EP | 2 143 690 | 1/2010 | |
| WO | 88 00935 | 2/1988 | |
| WO | 2004 022673 | 3/2004 | |
| WO | 2004 108609 | 12/2004 | |
| WO | WO 2004108609 A1 * | 12/2004 | ............... C02F 3/00 |
| WO | 2010 069516 | 6/2010 | |

* cited by examiner

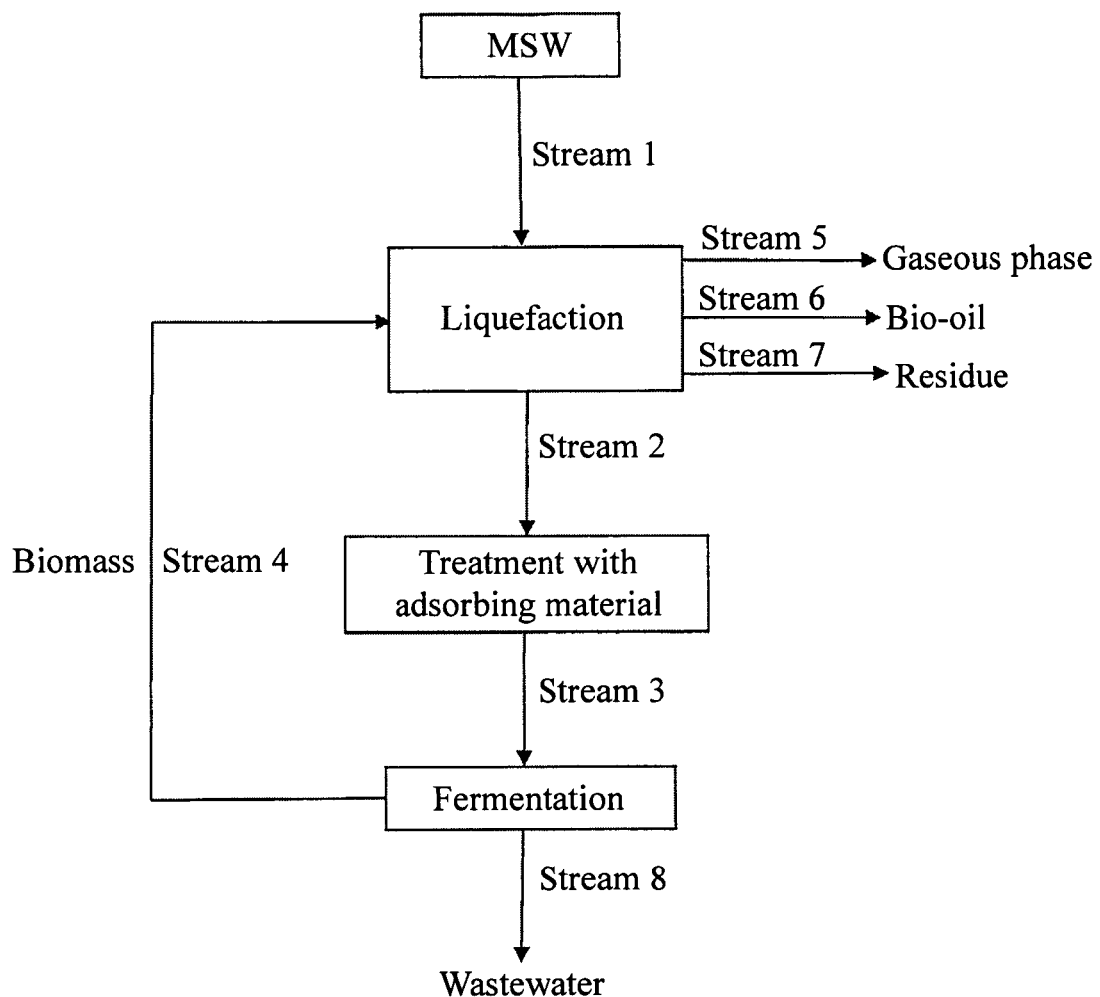

PROCESS FOR THE PRODUCTION OF BIO-OIL FROM MUNICIPAL SOLID WASTE

This application is a National Stage of PCT/IB11/000,693 filed Mar. 30, 2011 and claims the benefit of Italian patent application MI2010A 000646 filed Apr. 15, 2010.

The present invention relates to a process for the production of bio-oil from municipal solid waste (MSW).

More specifically, the present invention relates to a process for the production of bio-oil from municipal solid waste (MSW) which comprises subjecting said municipal solid waste to liquefaction, subjecting the aqueous phase obtained from said liquefaction to a treatment with at least one adsorbing material, subjecting the aqueous phase obtained from said treatment with at least one adsorbing material to fermentation, and subjecting the biomass obtained from said fermentation to said liquefaction.

The bio-oil (or bio-crude) thus obtained can be advantageously used in the production of biofuels which can be used as such, or mixed with other fuels, for motor vehicles. Alternatively, said bio-oil (or bio-crude) can be used as such (bio-combustible) or mixed with fossil combustibles (combustible oil, coal, etc.) for the generation of electric energy or heat.

The use of biomasses, in particular biomasses of a vegetal origin, for energy purposes, for example as raw material for the production of biocombustibles, or of components which can be added to fuels, is known in the art. Biomasse can, therefore, represents a source of renewable energy as an alternative to the traditional raw materials of a fossil origin normally used in the production of combustibles.

The use of said biomasses, however, can remove precious food resources for animal and/or human use.

Efforts have therefore been made in the art to use waste and/or municipal, industrial and/or agricultural residues for energy purposes.

U.S. Pat. No. 4,618,736, for example, describes a process for the production of hydrocarbons from a cellulose material comprising the steps of: forming a suspension of cellulose material in a polycyclic liquid hydrogen-donor compound, said suspension containing an amount of water equal to at least 5% by weight, but not more than approximately 10% by weight, with respect to the weight of the cellulose material; subjecting the suspension to a temperature higher than 200° C. and at a pressure increasing up to at least 1,000 psi, in the presence of hydrogen, in order to obtain the hydrogenation of the cellulose material and to produce a mixture of gaseous, liquid and solid hydrocarbons having an oxygen content lower than 10% by weight and a calorific value higher than 15,000 Btu/lb; separating the hydrocarbons mixture into three phases: gaseous, liquid and solid; and recovering said polycyclic liquid hydrogen-donor compound from the liquid phase and recycling it to the treatment of the cellulose material. Said cellulose material can derive from household or municipal waste or from vegetables. Said polycyclic liquid hydrogen donor compound is preferably tetralin.

American patent U.S. Pat. No. 4,670,613 describes a process for producing liquids containing hydrocarbons which essentially consists in introducing a biomass into a reaction zone, in the presence of water, at a pressure higher than the partial vapour pressure of the water and at a temperature of at least 300° C. and leaving said biomass in the reaction zone for more than 30 seconds; separating the solids from the fluid leaving the reaction zone and maintaining the fluid remaining in this zone in a single phase; and subsequently separating the liquids from the remaining fluid. Said biomass can be selected from a large range of biomasses of different origins, such as, for example, biomasses of a vegetal origin, biomasses deriving from agricultural waste, or from municipal waste.

Goudriaan et al. in "*Chemical Engineering Science*" (1990), Vol. 45, No. 8, pages 2729-2734 describe the process known as HTU or "HydroThermal Upgrading". This process allows biomass coming from energy crops to be converted into liquid fuel (e.g. bio-oil) which comprises treating the biomass in the presence of water, at a temperature higher than 300° C., for a time ranging from 5 to 15 minutes, at a pressure of 180 bar.

American patent U.S. Pat. No. 7,262,331 describes a process for continuously producing hydrocarbons having an improved energy density from biomass, comprising: a first step, in which an aqueous feed containing biomass, not pre-heated or pre-heated to a temperature ranging from 50° C. to 95° C., is subjected to treatment which comprises bringing said feed, in a single step, from a pressure of 5 bar or less, to a pressure ranging from 100 bar to 250 bar; a second step following the first step, in which the temperature of the feed under pressure, is increased from 95° C. or less to 180° C. or more, and the pressurized feed is maintained at a temperature not higher than 280° C. for a period of up to 60 minutes, thus forming a reaction mixture; a reaction step in which the reaction mixture is heated for a period of up to 60 minutes to a temperature higher than 280° C. Said biomass can be selected from biomass/water mixtures coming from the aerobic or anaerobic fermentation of industrial or municipal waste having a water/biomass ratio ranging from 4 to 5. Biomass deriving from agricultural waste, or household and municipal biowaste having a water/biomass ratio ranging from 1 to 4, can also be used.

The above processes however can have various drawbacks.

The high temperatures and the high pressures, for example, normally required for obtaining suitable yields in the process known as HTU or "Hydro Thermal Upgrading" require the use of specific equipment, normally made of special metal alloys capable of operating at said high temperatures and, in particular, at said high pressures, and a high energy consumption, with a consequent increase in the production costs.

Furthermore, by operating according to the processes described above, a part of organic material included in the biomass remains dissolved in the aqueous phase coming from the thermal treatment of said biomass with a consequent lower yield of hydrocarbons.

The Applicant considered the problem of finding a process for the production of bio-oil from municipal solid waste which allows an improvement in the yield of bio-oil. In particular, the Applicant considered the problem of finding a process capable of using organic material which, as indicated above, remains dissolved in the aqueous phase coming from the thermal treatment of said biomass.

The Applicant has now found that the production of bio-oils from municipal solid waste (i.e. the conversion of biomass into usable liquid products, for example, biocombustibles and/or biofuels), in particular from the organic fraction of municipal solid waste, can be advantageously carried out by means of a process which comprises subjecting said municipal solid waste to liquefaction, subjecting the aqueous phase obtained from said liquefaction to a treatment with at least one adsorbing material, subjecting the aqueous phase obtained from said treatment with at least one adsorbing material to fermentation, and subjecting the biomass obtained from said fermentation to said liquefaction.

In particular, the Applicant has found that the possibility of using the aqueous phase containing a part of the organic material deriving from municipal solid waste subjected to liquefaction, allows an increase in the yield of bio-oil.

Furthermore, the Applicant has found that said process allows a good yield of bio-oil to be obtained even when operating under much milder temperature and pressure conditions with respect to those adopted in the processes described in the known art, in particular under milder pressure conditions, with a consequent decrease in the production costs.

The bio-oil (or bio-crude) thus obtained can be advantageously used in the production of biofuels which can be used as such or mixed with other fuels, for motor vehicles. Alternatively, said bio-oil (or bio-crude) can be used as such (bio-combustible) or mixed with fossil combustibles (combustible oil, coal, etc.) for the generation of electric energy or heat.

An object of the present invention therefore relates to a process for the production of bio-oil from municipal solid waste comprising the following steps:
a) subjecting said municipal solid waste to liquefaction obtaining a mixture including an oily phase consisting of bio-oil, a solid phase and a first aqueous phase;
b) subjecting the first aqueous phase obtained in the liquefaction step (a) to a treatment with at least one adsorbing material obtaining a second aqueous phase;
c) subjecting the second aqueous phase obtained in the treatment step (b) with at least one adsorbing material to fermentation obtaining a biomass;
d) subjecting the biomass obtained in the fermentation step (c) to said liquefaction step (a).

It should be noted that from the liquefaction of the biomass obtained in the fermentation step (c), a further oily phase consisting of bio-oil is obtained, and consequently an increase in the yield of bio-oil.

It should also be noted that, even when operating under much milder operative temperature and pressure conditions with respect to those adopted in the processes described in the known art, in particular under milder pressure conditions, the additional oily phase consisting of bio-oil obtained from the liquefaction of the biomass obtained in the fermentation step (c), in any case allows good bio-oil yields to be obtained.

For the purposes of the present description and of the following claims, the definitions of the numerical ranges always include the extremes, unless otherwise specified.

In accordance with a preferred embodiment of the present invention, said municipal solid waste can be selected, for example, from organic material coming from sorted waste collection, organic material selected from unsorted municipal solid waste or mixtures thereof; or mixtures of said organic material with pruning cuttings and/or agricultural residues.

In accordance with a further preferred embodiment of the present invention, said municipal solid waste can be used in a mixture with other materials, such as, for example:
primary and biological sludge produced in wastewater purification plants;
residues and/or scraps deriving from agricultural and/or zootechnic activities;
residues and/or scraps deriving from the agro-food industry;
residues and/or scraps deriving from agricultural processing, from forestation and/or from silviculture;
or mixtures thereof.

In accordance with a preferred embodiment of the present invention, said municipal solid waste, as such or in a mixture with other materials, can be treated by subjecting it to a preliminary grinding or sizing process before being subjected to said liquefaction step (a).

In accordance with a preferred embodiment of the present invention, said municipal solid waste are wet. Said municipal solid waste preferably can have a water content higher than or equal to 50% by weight, preferably ranging from 55% by weight to 80% by weight, with respect to the total weight of said municipal solid waste.

In accordance with a preferred embodiment of the present invention, said liquefaction step (a) can be carried out at a temperature ranging from 150° C. to 350° C., preferably ranging from 200° C. to 320° C.

In accordance with a preferred embodiment of the present invention, said liquefaction step (a) can be carried out at a pressure ranging from 5 bar to 170 bar, preferably ranging from 15 bar to 115 bar.

In accordance with a preferred embodiment of the present invention, said liquefaction step (a) can be carried out for a time ranging from 5 minutes to 240 minutes, preferably ranging from 15 minutes to 90 minutes.

Said liquefaction step (a) can be carried out in reactors known in the art such as, for example, autoclaves.

Said liquefaction step (a) can be carried out by operating in different ways such as, for example, "batchwise", or in continuous.

Considering that the thermal energy necessary in said liquefaction step (a) can be partially or totally obtained from the heat recovery or from the combustion of traditional energy vectors, for example, methane gas, LPG, mineral oil, coal, etc., it is not excluded that the thermal energy can derive from other renewable sources, such as, for example solar, or biomasses.

The oily phase, the solid phase and the first aqueous phase included in the mixture obtained in said step (a), can be separated by techniques known in the art, such as, for example, gravitational separation (e.g., sedimentation, decanting), filtration, centrifugation. Said phases are preferably separated by gravitational separation.

During said liquefaction step (a) a gaseous phase is also formed, equal to about 10% by weight-25% by weight with respect to the weight (dry weight) of said municipal solid waste. Said gaseous phase is mainly composed of carbon dioxide (about 80% in moles-95% in moles) and of a mixture of hydrocarbons having from 1 to 4 carbon atoms or of other gases (about 5% in moles-20% in moles). Said gaseous phase, after separation, separation which can be carried out, for example, by depressurizing the pressurized vessel in which said liquefaction step (a) is carried out, before sending the mixture obtained (oily phase+solid phase+first aqueous phase) in said liquefaction step (a) to separation, is generally sent to further treatments in order to upgrade its combustible organic component.

The solid phase obtained after separation generally comprises ashes and inert products. Said solid phase can be used, for example, as inorganic starting material in the building industry, or in the ceramics industry.

The first aqueous phase obtained after separation comprises part of the organic material included in said municipal solid waste. Said first aqueous phase can generally have a content of organic material higher than or equal to 25% by weight, preferably ranging from 30% to 50% by weight, with respect to the total weight of the dry fraction of said municipal solid waste.

In accordance with a preferred embodiment of the present invention, said treatment step (b) with at least one adsorbing material can be carried out at a temperature ranging from 20° C. to 150° C., preferably ranging from 30° C. to 100° C.

In accordance with a preferred embodiment of the present invention, said treatment step (b) with at least one adsorbing material can be carried out at a pressure ranging from 0.5 bar to 10 bar, preferably ranging from 1 bar to 2 bar.

In accordance with a preferred embodiment of the present invention, said treatment step (b) with at least one adsorbing material can be carried out for a time ranging from 10 minutes to 6 hours, preferably ranging from 30 minutes to 4 hours.

For the purposes of the present description and of the following claims, the term "adsorbing material" relates to a natural or synthetic material capable of withholding organic substances on its surface through physical or chemical ("chemisorption") means.

In accordance with a preferred embodiment of the present invention, said adsorbing material can be selected, for example, from: zeolites, as such or chemically modified; clays, as such or chemically modified; mesoporous materials, as such or chemically modified; ion exchange resins; or mixtures thereof.

For the purposes of the present invention, said zeolites can be selected, for example, from: natural zeolites, as such or chemically modified, such as, for example, clinoptilolite, mordenite, phillipsite, cabasite, erionite, faujasite, stilbite, or mixtures thereof; synthetic zeolites, as such or chemically modified, such as, for example, ZSM-5 zeolite, H-ZSM5 zeolite, zeolite A, zeolite X, zeolite Y, zeolite L, beta zeolite, or mixtures thereof; or mixtures thereof.

For the purposes of the present invention, said clays can be selected, for example, from: natural or synthetic clays, as such or chemically modified, such as, for example, sepiolite, bentonite, hectorite, montmorillonite, attapulgite, halloysite, kaolinite, or mixtures thereof.

For the purposes of the present invention, said mesoporous materials can be selected, for example, from: alumino-silicates, as such or chemically modified, having an average pore diameter ranging from 20 Å to 500 Å, such as, for example, MCM-41, MCM-48, of Mobil, or mixtures thereof.

For the purposes of the present invention, said ion exchange resins can be selected, for example, from: resins containing active groups (for example, sulfonic groups, carboxyl groups, phenol groups, amino-substituted groups) such as, for example, resins of the Amberjet® series or of the Amberlite® series of Rohm and Haas, or mixtures thereof.

In accordance with a preferred embodiment of the present invention, said adsorbing material can be added to said first aqueous phase in an amount ranging from 0.5% by weight to 50% by weight, preferably from 5% by weight to 15% by weight, with respect to the total weight of second aqueous phase.

Said treatment step (b) with at least one adsorbing material can be carried out in reactors known in the art, such as, for example, fixed bed reactors, slurry reactors.

Said treatment step (b) with at least one adsorbing material can be carried out operating in different ways, such as, for example, batchwise, or in continuous.

It should be pointed out that said treatment with at least one adsorbing material does not cause a significant reduction in the carbon source present in the first aqueous phase. Said second aqueous phase generally has a total organic carbon content (TOC) equal to about 90% with respect to the total organic carbon content (TOC) of said first aqueous phase. Said total organic carbon content (TOC) was determined by combustion by means of a TOC analyzer capable of determining the total carbon content (TC) and the inorganic carbon content (IC) from which the total organic carbon content (TOC) is calculated, by difference.

It should be noted that the content of organic material of said second aqueous phase remains substantially unvaried with respect to that of said first aqueous phase.

In accordance with a preferred embodiment of the present invention, said fermentation step (c) can be carried out in the presence of at least one oleaginous yeast.

In accordance with a preferred embodiment of the present invention, said oleaginous yeast can be selected from: *Rhodotorula glutinis, Rhodotorula gracilis, Rhodotorula graminis, Lypomices starkeyi, Lypomices lipofer, Trigonopsis variabilis, Candida kefyr, Candida curvata, Candida lipolytica, Torulopsis* sp., *Pichia stipitis, Criptococcus albidus, Criptococcus* sp., or mixtures thereof.

In accordance with a further preferred embodiment of the present invention, said fermentation step (c) can be carried out in the presence of at least one microbial consortium isolated from the first aqueous phase obtained in said liquefaction step (a), or from the second aqueous phase obtained in said treatment step (b) with at least one adsorbing material. For this purpose, the first aqueous phase obtained in said liquefaction step (a), or the second aqueous phase obtained in said treatment step (b) with at least one adsorbing material, is kept under stirring, in air, for 10 days, at room temperature (25° C.)

In accordance with a preferred embodiment of the present invention, said fermentation step (c) can be carried out at a temperature ranging from 20° C. to 40° C., preferably ranging from 25° C. to 35° C.

In accordance with a preferred embodiment of the present invention, said fermentation step (c) can be carried out for a time ranging from 10 hrs to 120 hrs, preferably from 24 hrs to 100 hrs.

In accordance with a preferred embodiment of the present invention, said fermentation step (c) can be carried out at a pH ranging from 4.5 to 7.5, preferably ranging from 5 to 7.

In order to maintain the pH within the desired ranges, an aqueous solution of at least one inorganic base, such as, for example, sodium hydroxide, potassium hydroxide, calcium hydroxide, magnesium hydroxide, or mixtures thereof, can be added to the culture medium for the fermentation, in such an amount so as to obtain the desired pH.

Said fermentation step (c) can be carried out operating in different ways such as, for example, batchwise (fed-batch fermentation), or in continuous.

Before being used in said fermentation step (c), said oleaginous yeast can be cultivated in a culture medium known in the art such as, for example, YEPG, Nutrient Broth.

Said fermentation step (c) can be carried out in fermenters known in the art.

In order to concentrate the yeast cells in the fermented biomass obtained in said fermentation step (c), said biomass, before being subjected to said liquefaction step (a), can be subjected to a thickening treatment.

In accordance with a preferred embodiment of the present invention, at the end of said fermentation step (c), said biomass, before being subjected to said liquefaction step (a), can be subjected to a thickening treatment. In this phase, the concentration of the yeast cells is brought to values ranging from 5% by weight to 50% by weight, preferably from 15% by weight to 30% by weight, with respect to the total weight (dry weight) of the biomass. Said thickening can be carried out by means of techniques known in the art such as, for example, sedimentation, decanting, flocculation, filtration, and the like.

After thickening, the biomass is subjected to said liquefaction step (a).

An aqueous waste is also obtained from said thickening, which can be optionally cooled to a temperature ranging from room temperature (25° C.) to 50° C., and sent to a subsequent treatment such as, for example, biological aerobic or anaerobic treatment.

As already mentioned above, a further oily phase is obtained from the liquefaction of said biomass, consisting of bio-oil which will be recovered together with the oily phase consisting of bio-oil obtained from the liquefaction of said municipal solid waste.

A further solid phase, a further aqueous phase and a further gaseous phase are also obtained from the liquefaction of said biomass, which will be recovered together with the solid phase, the aqueous phase and the gaseous phase, respectively, obtained by the liquefaction of said municipal solid waste.

The process object of the present invention allows bio-oil to be produced with an overall yield ranging from 15% to 50%, said yield being calculated with respect to the weight of the dry fraction of the initial municipal solid waste (MSW).

It should be noted that the process, object of the present invention, thanks to the use of the second aqueous phase obtained in the treatment step (b) with at least one adsorbing material, allows an increase in the yield of bio-oil to be obtained, with respect to the liquefaction step (a) alone, ranging from 5% to 30%, said increase in the yield being calculated with respect to the weight of the dry fraction of the initial municipal solid waste (MSW).

The bio-oil obtained with the above process can be sent to the subsequent processing phases in order to transform it, for example, into biofuel by means of treatments known in the art such as, for example, hydrogenation or cracking.

The present invention will now be illustrated through an illustrative embodiment with reference to FIG. 1 provided hereunder.

According to a typical embodiment of the process object of the present invention, the municipal solid waste (MSW) (Stream 1) are subjected to liquefaction obtaining a mixture (not represented in FIG. 1) comprising three phases: an oily phase consisting of bio-oil, a solid phase (i.e. residue) and a first aqueous phase. Said mixture is sent to a phase separation section (not represented in FIG. 1) in order to separate the above three phases obtaining: an oily phase consisting of bio-oil (Stream 6), a solid phase (i.e. residue) (Stream 7) comprising ashes, inert products, and a first aqueous phase (Stream 2).

Said first aqueous phase (Stream 2) is subjected to treatment with at least one adsorbing material (e.g., natural or synthetic zeolite, clay) obtaining a second aqueous phase (Stream 3).

Said second aqueous phase (Stream 3) is subjected to fermentation in the presence of an oleaginous yeast (e.g., *Rhodotorula graminis* DBVPG 4620), or of a microbial consortium isolated from the first aqueous phase obtained in the liquefaction step (a), or of a microbial consortium isolated from the second aqueous phase obtained in the treatment step (b) with at least one adsorbing material, as described above.

At the end of the fermentation, a biomass is obtained, which is subjected to a thickening treatment (not represented in FIG. 1) in order to concentrate the cells of said oleaginous yeast in said biomass in order to obtain concentration values preferably ranging from 5% by weight to 30% by weight with respect to the total weight (dry weight) of said biomass. An aqueous sludge (Stream 8) is also obtained from said thickening treatment, which can be sent to a subsequent treatment such as, for example, biological aerobic or anaerobic treatment (not represented in FIG. 1).

At the end of the thickening treatment, the biomass (Stream 4) is subjected to liquefaction together with the municipal solid waste. The further oily phase consisting of bio-oil obtained from the liquefaction of said biomass is recovered in (Stream 6).

A further solid phase, a further aqueous phase and a further gaseous phase are also obtained from the liquefaction of said biomass, which are recovered in (Stream 7), (Stream 2) and (Stream 5), respectively.

As described above, during the liquefaction step (a), a gaseous phase (Stream 5) is also produced, comprising $CO_2$, gaseous hydrocarbons having from 1 to 4 carbon atoms, or other gases, which can be separated, for example, by depressurization of the pressurized vessel in which said liquefaction is carried out, before sending the mixture (oily phase+solid phase+first aqueous phase) obtained after liquefaction to the phase separation section. The gaseous phase thus obtained (Stream 5) can be sent to further treatments in order to upgrade its combustible organic component.

The bio-oil thus obtained can be sent to subsequent processing phases to be transformed, for example, into biofuel by means of hydrogenation or cracking treatment, for example (not represented in FIG. 1)

Some illustrative and non-limiting examples are provided hereunder for a better understanding of the present invention and for its embodiment.

EXAMPLE 1

Comparative 500 g of wet organic fraction of municipal solid waste (MSW) are fed, with a suitable dosage system, into a stirred 1 liter autoclave. The dry weight of this fraction proves to be equal to 25% by weight (125 g).

After creating an inert atmosphere inside the autoclave by washings with nitrogen, the autoclave is rapidly heated in order to reach the internal temperature of 310° C.: it is kept, under stirring, under these conditions, for 1 hour, observing that the pressure inside the autoclave reaches the maximum pressure of 110 bar.

The autoclave is then rapidly cooled to 80° C. and the gaseous phase is separated. Said gaseous phase is analyzed separately by gaschromatographic techniques, and proves to be equal to 22.5 g (18% by weight of the dry fraction of the initial MSW). The analysis showed that 90% of the gaseous phase consists of carbon dioxide.

The reaction mixture thus obtained is separated, under heating, in a gravitational separator obtaining three phases:
- an oily phase consisting of bio-oil which, once anhydrified, proves to be equal to 43.7 g (35% by weight of the dry fraction of the initial MSW);
- a solid phase consisting of a solid residue equal to 18.8 g (15% by weight of the dry fraction of the initial MSW);
- an aqueous phase equal to 415 g having an USW content equal to 40.0 g (32% by weight of the dry fraction of the initial MSW).

EXAMPLE 2

500 g of wet organic fraction of municipal solid waste (MSW) are fed, with a suitable dosage system, into a stirred 1 liter autoclave. The dry weight of this fraction proves to be equal to 25% by weight (125 g).

After creating an inert atmosphere inside the autoclave by washings with nitrogen, the autoclave is rapidly heated in order to reach the internal temperature of 310° C.: it is kept, under stirring, under these conditions, for 1 hour, observing that the pressure inside the autoclave reaches the maximum pressure of 110 bar.

The autoclave is then rapidly cooled to 80° C. and the gaseous phase is separated. Said gaseous phase is analyzed separately by gaschromatographic techniques, and proves to be equal to 22 g (17% by weight of the dry fraction of the initial MSW). The analysis showed that 90% of the gaseous phase consists of carbon dioxide.

The reaction mixture thus obtained is separated, under heat, in a gravitational separator obtaining three phases:
- an oily phase consisting of bio-oil which, once anhydrified, proves to be equal to 42 g (33.6% by weight of the dry fraction of the initial MSW);
- a solid phase consisting of a solid residue equal to 18.8 g (15% by weight of the dry fraction of the initial MSW);
- a first aqueous phase equal to 416 g having a MSW content equal to 41.7 g (32% by weight of the dry fraction of the initial MSW).

Said first aqueous phase is transferred to a stirred, thermostat-regulated, 1-liter glass flask. A clay (Grade F20 of Engelhard) is added in an amount equal to 10 g per 100 g of the aqueous phase. The mixture obtained is brought to 80° C., under mild stirring and is maintained under these conditions for about 3 hours. At the end, the mixture is filtered under heat in order to recover a second aqueous phase which proved to be equal to 395 g.

Said second aqueous phase is used entirely and without any dilution as growth medium in the subsequent fermentation step: yeast extract only is added at a concentration of 1 g/l as vitamin source and the pH is adjusted to a value of 6.5 by the addition of an aqueous solution of potassium hydroxide (KOH) 0.1 M. Said second aqueous phase is subsequently fed to a fermenter having a useful volume of 1 liter and inoculated with a strain of *Rhodotorula graminis* DBVPG 4620 previously cultivated in a YEPG yeast medium (inoculum equal to 5 g/l—dry weight).

The fermentation is carried out at a temperature of 30° C. and with a stirring equal to 170 rpm. After 70 hours of fermentation, the biomass is recovered by centrifugation (5,000 rpm, for 30 minutes) obtaining 56 g of wet biomass containing 20% by weight of cells (dry weight equal to 11.2 g). The determination of the lipid content is carried out by means of the phospho-vanillin method, using a Spinreact Kit. The centrifuged cells are digested with sulfuric acid 0.1 M and the lysate obtained is reacted with a solution of phospho-vanillin which forms a coloured complex with the fatty acids. The dosage is carried out by reading the spectrophotometer at 540 nm and referring to a calibration line. The lipid content proved to be equal to 5.1% by weight (with respect to the dry weight of the cells).

The biomass thus obtained is fed to the above mentioned stirred 1 liter autoclave, together with 500 g of organic fraction of municipal solid waste (MSW): the liquefaction is carried out under the same operating conditions described above. After analogous separation treatment, a further 4.8 g of bio-oil are thus obtained, which in total lead to the formation of 46.8 g of bio-oil with an increase in the bio-oil yield equal to 11.4%.

EXAMPLE 3

500 g of wet organic fraction of municipal solid waste (MSW) are fed, with a suitable dosage system, into a stirred 1 liter autoclave. The dry weight of this fraction proves to be equal to 25% by weight (125 g).

After creating an inert atmosphere inside the autoclave by washings with nitrogen, the autoclave is rapidly heated in order to reach the internal temperature of 310° C.: it is kept under stirring, under these conditions, for 1 hour, observing that the pressure inside the autoclave reaches the maximum pressure of 108 bar.

The autoclave is then rapidly cooled to 80° C. and the gaseous phase is separated. Said gaseous phase is analyzed separately by gaschromatographic techniques, and proves to be equal to 20.5 g (16% by weight of the dry fraction of the initial MSW). The analysis showed that 89% of the gaseous phase consists of carbon dioxide.

The reaction mixture thus obtained is separated, under heat, in a gravitational separator obtaining three phases:
- an oily phase consisting of bio-oil which, once anhydrified, proves to be equal to 40 g (32% by weight of the dry fraction of the initial MSW);
- a solid phase consisting of a solid residue equal to 18.7 g (15% by weight of the dry fraction of the initial MSW);
- a first aqueous phase equal to 421 g having a MSW content equal to 46.3 g (37% by weight of the dry fraction of the initial USW).

Said first aqueous phase is transferred to a stirred, thermostat-regulated, 1-liter glass flask. A natural clay (Sepiolite 30/60 of Tolsa) is added in an amount equal to 10 g per 100 g of the aqueous phase. The mixture obtained is brought to 80° C., under mild stirring and is maintained under these conditions for about 3 hours. At the end, the mixture is filtered under heat in order to recover a second aqueous phase which proved to be equal to 400 g.

Said second aqueous phase is used entirely and without any dilution as growth medium in the subsequent fermentation step: yeast extract only is added at a concentration of 1 g/l as vitamin source and the pH is adjusted to a value of 6.5 by the addition of an aqueous solution of potassium hydroxide (KOH) 0.1 M. Said second aqueous phase is subsequently fed to a fermenter having a useful volume of 1 liter and inoculated with a strain of *Rhodotorula graminis* DBVPG 4620 previously cultivated in a YEPG yeast medium (inoculum equal to 5 g/l—dry weight).

The fermentation is carried out at a temperature of 30° C. and with a stirring equal to 170 rpm. After 70 hours of fermentation, the biomass is recovered by centrifugation (5,000 rpm, for 30 minutes) obtaining 69.7 g of wet biomass containing 20% by weight of cells (dry weight equal to 13.9 g). The determination of the lipid content is carried out by means of the phospho-vanillin method, using a Spinreact Kit. The centrifuged cells are digested with sulfuric acid 0.1 M and the lysate obtained is reacted with a solution of phospho-vanillin which forms a coloured complex with the fatty acids. The dosage is carried out by reading the spectrophotometer at 540 nm and referring to a calibration line. The lipid content proved to be equal to 16.2% by weight (with respect to the dry weight of the cells).

The biomass thus obtained is fed to the above mentioned stirred 1 liter autoclave, together with 500 g of organic fraction of municipal solid waste (MSW): the liquefaction is carried out under the same operating conditions described above. After analogous separation treatment, a further 6.9 g of bio-oil are thus obtained, which in total lead to the formation of 46.9 g of bio-oil with an increase in the bio-oil yield equal to 17.2%.

EXAMPLE 4

500 g of wet organic fraction of municipal solid waste (MSW) are fed, with a suitable dosage system, into a stirred 1 liter autoclave. The dry weight of this fraction proves to be equal to 25% by weight (125

After creating an inert atmosphere inside the autoclave by washings with nitrogen, the autoclave is rapidly heated in order to reach the internal temperature of 310° C.: it is kept under stirring, under these conditions, for 1 hour, observing that the pressure inside the autoclave reaches the maximum pressure of 110 bar.

The autoclave is then rapidly cooled to 80° C. and the gaseous phase is separated. Said gaseous phase is analyzed separately by gaschromatographic techniques, and proves to be equal to 22.1 g (17% by weight of the dry fraction of the initial MSW). The analysis showed that 90% of the gaseous phase consists of carbon dioxide.

The reaction mixture thus obtained is separated, under heat, in a gravitational separator obtaining three phases:
- an oily phase consisting of bio-oil which, once anhydrified, proves to be equal to 42.5 g (34% by weight of the dry fraction of the initial MSW);
- a solid phase consisting of a solid residue equal to 17 g (13.5% by weight of the dry fraction of the initial MSW);
- a first aqueous phase equal to 419 g having a MSW content equal to 44.2 g (35.5% by weight of the dry fraction of the initial MSW).

Said first aqueous phase is transferred to a stirred, thermostat-regulated, 1-liter glass flask. A synthetic zeolite (HZSM-5 of Zeolyst) is added in an amount equal to 10 g per 100 g of the aqueous phase. The mixture obtained is brought to 80° C., under mild stirring and is maintained under these conditions for about 3 hours. At the end, the mixture is filtered under heat in order to recover a second aqueous phase which proved to be equal to 402 g.

Said second aqueous phase is used entirely and without any dilution as growth medium in the subsequent fermentation step: yeast extract only is added at a concentration of 1 g/l as vitamin source and the pH is adjusted to a value of 6.5 by the addition of an aqueous solution of potassium hydroxide (KOH) 0.1M. Said second aqueous phase is subsequently fed to a fermenter having a useful volume of 1 liter and inoculated with a strain of *Rhodotorula graminis* DBVPG 4620 previously cultivated in a YEPG yeast medium (inoculum equal to 5 g/l—dry weight).

The fermentation is carried out at a temperature of 30° C. and with a stirring equal to 170 rpm. After 70 hours of fermentation, the biomass is recovered by centrifugation (5,000 rpm, for 30 minutes) obtaining 47.5 g of wet biomass containing 20% by weight of cells (dry weight equal to 9.5 g). The determination of the lipid content is carried out by means of the phospho-vanillin method, using a Spinreact Kit. The centrifuged cells are digested with sulfuric acid 0.1 M and the lysate obtained is reacted with a solution of phospho-vanillin which forms a coloured complex with the fatty acids. The dosage is carried out by reading the spectrophotometer at 540 nm and referring to a calibration line. The lipid content proved to be equal to 18% by weight (with respect to the dry weight of the cells).

The biomass thus obtained is fed to the above mentioned stirred 1 liter autoclave, together with 500 g of organic fraction of municipal solid waste (MSW): the liquefaction is carried out under the same operating conditions described above. After analogous separation treatment, a further 4.8 g of bio-oil are thus obtained, which in total lead to the formation of 47.3 g of bio-oil with an increase in the bio-oil yield equal to 11.3%.

EXAMPLE 5

500 g of wet organic fraction of municipal solid waste (MSW) are fed, with a suitable dosage system, into a stirred 1 liter autoclave. The dry weight of this fraction proves to be equal to 25% by weight (125 g).

After creating an inert atmosphere inside the autoclave by washings with nitrogen, the autoclave is rapidly heated in order to reach the internal temperature of 310° C.: it is kept under stirring, under these conditions, for 1 hour, observing that the pressure inside the autoclave reaches the maximum pressure of 110 bar.

The autoclave is then rapidly cooled to 80° C. and the gaseous phase is separated. Said gaseous phase is analyzed separately by gaschromatographic techniques, and proves to be equal to 21.9 g (17.5% by weight of the dry fraction of the initial MSW). The analysis showed that 91% of the gaseous phase consists of carbon dioxide.

The reaction mixture thus obtained is separated, under heat, in a gravitational separator obtaining three phases:
- an oily phase consisting of bio-oil which, once anhydrified, proves to be equal to 41.5 g (33% by weight of the dry fraction of the initial MSW);
- a solid phase consisting of a solid residue equal to 18 g (14.4% by weight of the dry fraction of the initial MSW);
- a first aqueous phase equal to 418.5 g having a MSW content equal to 44.2 g (43.6% by weight of the dry fraction of the initial USW).

Said first aqueous phase is transferred to a stirred, thermostat-regulated, 1-liter glass flask. A natural zeolite (clinoptilolite coming from Turkey) is added in an amount equal to 10 g per 100 g of the aqueous phase. The mixture obtained is brought to 80° C., under mild stirring and is maintained under these conditions for about 3 hours. At the end, the mixture is filtered under heat in order to recover a second aqueous phase which proved to be equal to 397 g.

Said second aqueous phase is used entirely and without any dilution as growth medium in the subsequent fermentation step: yeast extract only is added at a concentration of 1 g/l as vitamin source and the pH is adjusted to a value of 6.5 by the addition of an aqueous solution of potassium hydroxide (KOH) 0.1M. Said second aqueous phase is subsequently fed to a fermenter having a useful volume of 1 liter and inoculated with a strain of *Rhodotorula graminis* DBVPG 4620 previously cultivated in a YEPG yeast medium (inoculum equal to 5 g/l—dry weight).

The fermentation is carried out at a temperature of 30° C. and with a stirring equal to 170 rpm. After 70 hours of fermentation, the biomass is recovered by centrifugation (5,000 rpm, for 30 minutes) obtaining 40 g of wet biomass containing 20% by weight of cells (dry weight equal to 8 g). The determination of the lipid content is carried out by means of the phospho-vanillin method, using a Spinreact Kit. The centrifuged cells are digested with sulfuric acid 0.1 M and the lysate obtained is reacted with a solution of phospho-vanillin which forms a coloured complex with the fatty acids. The dosage is carried out by reading the spectrophotometer at 540 nm and referring to a calibration line. The lipid content proved to be equal to 10% by weight (with respect to the dry weight of the cells).

The biomass thus obtained is fed to the above mentioned stirred 1 liter autoclave, together with 500 g of organic fraction of municipal solid waste (MSW): the liquefaction is carried out under the same operating conditions described above. After analogous separation treatment, a further 3.7 g of bio-oil are thus obtained, which in total lead to the formation of 45.2 g of bio-oil with an increase in the bio-oil yield equal to 9%.

The invention claimed is:

1. A process for producing bio-oil from municipal solid waste, the process comprising:
   a) liquifying the municipal solid waste, to obtain a mixture comprising an oily phase comprising bio-oil, a solid phase, and a first aqueous phase;
   b) treating the first aqueous phase obtained in a) with an adsorbing material, to obtain a second aqueous phase;
   c) fermenting the second aqueous phase obtained in b), to obtain a biomass;
   d) subjecting the biomass obtained in c) to the liquifying a).

2. The process of claim 1, wherein municipal solid waste is an organic material from a sorted waste collection, an organic material from unsorted municipal solid waste, or a mixture thereof; or a mixture comprising the organic material and pruning cuttings, agricultural residues, or a mixture thereof.

3. The process of claim 2, wherein the municipal solid waste is employed in a mixture comprising:
   primary and biological sludge produced in a wastewater purification plant;
   a residue, a scrap, or a mixture thereof from agricultural and/or zootechnic activities;
   a residue, a scrap, or a mixture thereof from an agro-food industry;
   a residue, a scrap, or a mixture thereof from agricultural processing, forestation, and/or silviculture;
   or any mixture thereof.

4. The process of claim 1, further comprising prior to a):
   preliminary grinding or sizing the municipal solid waste, as such or in a mixture comprising a further material.

5. The process of claim 1, wherein the municipal solid waste has a water content higher than or equal to 50% by weight, based on the total weight of the municipal solid waste.

6. The process of claim 5, wherein the municipal solid waste has a water content in a range from 55% by weight to 80% by weight, based on the total weight of the municipal solid waste.

7. The process of claim 1, wherein the liquifying (a) is carried out at a temperature in a range from 150° C. to 350° C.

8. The process of claim 7, wherein the liquifying (a) is carried out at a temperature in a range from 200° C. to 320° C.

9. The process of claim 1, wherein the liquifying (a) is carried out at a pressure in a range from 5 bar to 170 bar.

10. The process of claim 9, wherein the liquifying (a) is carried out at a pressure in a range from 15 bar to 115 bar.

11. The process of claim 1, wherein the liquifying (a) is carried out for a time in a range from 5 minutes to 240 minutes.

12. The process of claim 11, wherein the liquifying (a) is carried out for a time in a range from 15 minutes to 90 minutes.

13. The process of claim 1, wherein the oily phase, the solid phase, and the first aqueous phase in the mixture obtained in (a), are separated by gravitational separation, filtration, or centrifugation.

14. The process of claim 1, wherein the treating (b) is carried out at a temperature in a range from 20° C. to 150° C.

15. The process of claim 14, wherein the treating (b) is carried out at a temperature in a range from 30° C. to 100° C.

16. The process of claim 1, wherein the treating (b) is carried out at a pressure in a range from 0.5 bar to 10 bar.

17. The process of claim 16, wherein the treating (b) is carried out at a pressure in a range from 1 bar to 2 bar.

18. The process of claim 1, wherein the treating (b) is carried out for a time in a range from 10 minutes to 6 hours.

19. The process of claim 18, wherein the treating (b) is carried out for a time in a range from 30 minutes to 4 hours.

20. The process of claim 1, wherein said adsorbing material is:
   a zeolite, as such or chemically modified; a clay, as such or chemically modified; a mesoporous material, as such or chemically modified; an ion exchange resin; or any mixture thereof.

21. The process of claim 1, wherein said adsorbing material is added to the first aqueous phase in an amount ranging from 0.5% to 50% by weight, based on the total weight of the second aqueous phase.

22. The process of claim 21, wherein the adsorbing material is added to said first aqueous phase in an amount ranging from 5% to 15% by weight, based on the total weight of the second aqueous phase.

23. The process of claim 1, wherein the fermenting (c) is carried out in the presence of an oleaginous yeast.

24. The process of claim 23, wherein the oleaginous yeast is *Rhodotorula glutinis*, *Rhodotorula gracilis*, *Rhodotorula graminis*, *Lypomices starkeyi*, *Lypomices lipofer*, *Trigonopsis variabilis*, *Candida kefyr*, *Candida curvata*, *Candida lipolytica*, *Torulopsis* sp., *Pichia stipitis*, *Criptococcus albidus*, *Criptococcus* sp, or any mixture thereof.

25. The process of claim 1, wherein the fermenting (c) is carried out in the presence of a microbial consortium isolated from the first aqueous phase obtained in (a), or from the second aqueous phase obtained in (b) with an adsorbing material.

26. The process of claim 1, wherein the fermenting (c) is carried out at a temperature in a range from 20° C. to 40° C.

27. The process of claim 26, wherein the fermenting (c) is carried out at a temperature in a range from 25° C. to 35° C.

28. The process of claim 1, wherein the fermenting (c) is carried out for a time in a range from 10 hours to 120 hours.

29. The process of claim 28, wherein the fermenting (c) is carried out for a time in a range from 24 hours to 100 hours.

30. The process of claim 1, wherein the fermenting (c) is carried out at a pH in a range from 4.5 to 7.5.

31. The process of claim 30, wherein the fermenting (c) is carried out at a pH in a range from 5 to 7.

32. The process of claim 1, further comprising, after (c) and before (d):
   thickening the biomass.

* * * * *